United States Patent [19]
Tobe et al.

[11] 3,957,581
[45] May 18, 1976

[54] METHOD OF PRODUCING PEPTIDASE
[75] Inventors: Sadanobu Tobe, Tokyo; Ryuichi Miyajima; Koji Mitsugi, both of Yokohama, all of Japan
[73] Assignee: Ajinomoto Co., Inc., Tokyo, Japan
[22] Filed: Feb. 13, 1975
[21] Appl. No.: 549,832

[30] Foreign Application Priority Data
Feb. 18, 1974 Japan.................................. 49-19224

[52] U.S. Cl.................................. 195/65; 195/66 R
[51] Int. Cl.²......................................... C12D 13/10
[58] Field of Search............................ 195/65, 66 R

[56] References Cited
OTHER PUBLICATIONS
OKA et al., Archives Biochemistry & Biophysics, Vol. 156 pp. 552–559 (1973).

*Primary Examiner*—A. Louis Monacell
*Assistant Examiner*—Robert J. Warden
*Attorney, Agent, or Firm*—Hans Berman; Kurt Kelman

[57] ABSTRACT
Some strains of Cladosporium produce highly active peptidase. The peptidase can liberate most amino acids from proteins in high yields.

5 Claims, 2 Drawing Figures

METHOD OF PRODUCING PEPTIDASE

This invention relates to the preparation of peptidase by microorganisms.

When protein is hydrolyzed enzymatically, the protein conventionally is first hydrolyzed to peptides by protease and then further to amino acids by peptidase. There are many highly active proteases, but highly active peptidase was not known heretofore.

It is known that microorganisms, such as *Aspergillus oryzae*, *A. saitoi*, *Streptomyces griseus*, *S. sioyaensis* and *Bacillus subtilis*, produce peptidase, but the activity of the known peptidases is low.

It has now been found that new strains of Cladosporium produce highly active peptidase in a large amount in the culture broth.

Figure 1:
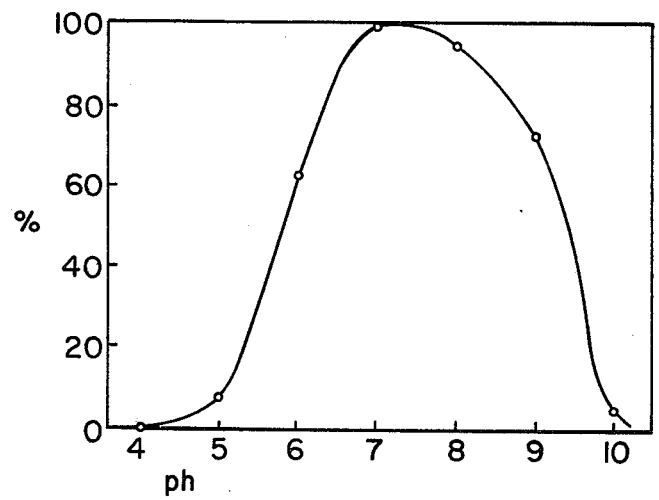
Figure 2:
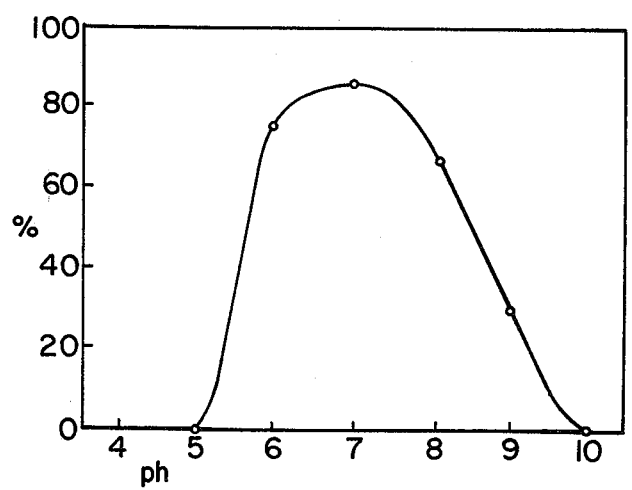

In the attached drawing,

FIG. 1 and FIG. 2 diagrammatically show the relationship between pH and the activity of the new peptidase.

The microorganisms which produce the peptidase are Cladosporium sp. AJ 6634 (FERM P-801) and Cladosporium sp. AJ 14113 (FERM P-2447). Microorganisms identified by FERM P-numbers are available from the Fermentation Research Institute, Agency of Industrial Science and Technology, Ministry for Industrial Trade and Industry, Chiba, Japan.

Microbial properties of Cladosporium sp. FERM P-801 are as follows:

1. Growth on various media

Glucose agar

Colonies on glucose agar (Glucose 5%, $KNO_3$ 0.2%, $KH_2PO_4$ 0.1%, $MgSO_4 \cdot 7H_2O$ 0.05%, agar 2%) develop restrictedly, attaining a diameter of 21–22 mm in 10 days at 25°C. They are velvety, cerebri-form at center, radial furrow at semi central area, consisting of tough-thick basal felt.

The color of the colonies is pale yellow orange at center, brownish white to white at margin at first, becoming brownish white to pale yellow orange. Exudates are not produced. Surrounding agar is slightly pale yellow orange at first, becoming light yellow orange. The reverse of the colonies is pale yellow orange to pale yellow.

At 30°C, colonies on glucose agar develop restrictedly, attaining a diameter of 27–29 mm in 10 days. They are thin, cerebri-form at center, radial furrow at semi central area, and velvety, flat, tough to soft at margin.

The color of the colonies is pale yellow orange at center, brownish white to white at margin. Exudates are not produced. Water soluble pigment is pale yellow orange. The reverse is pale yellow orange at first, becoming light brownish gray at center and pale yellow at margin.

Hyphae are septate, colorless, smooth, and 2–3 $\mu$m in diameter.

Conidial structures are tree-like, spread, and 50–100 $\mu$m in diameter.

Conidiophores arising laterally from the hyphae are smooth, colorless, septate, 20–100 $\mu$m × 2–3 $\mu$m, and often fusiform.

Blastospores are branched in chain predominantly in basal conidium, smooth, colorless, elliptical to ovate, and apiculate at one or both ends, 1.2–2.5(–3.0)×3–.5–6 $\mu$m at first, becoming widely elliptical or ovate, 2.0–3.8×4–6.5 $\mu$m.

Basal conidium is fusiform, denticulate, smooth, apiculate at one or both ends, 1.2–2.2×5–.5–13(–25) $\mu$m at first, becoming 2–3×7–17(–23) $\mu$m.

Blastospores and basal conidium are non septate unicell.

Malt agar

Colonies on malt agar develop restrictedly, attaining a diameter of 18–20 mm in 10 days at 25°C.

They are cerebri-form at center, velvety, flat at margin, and slightly tough-basal felt.

The color of colonies is pale orange at center, brownish white to white at margin at first, becoming pale yellow orange to white. Exudates are not produced. The reverse of the colonies is dull yellow orange.

Czapek-dox's agar:

Colonies on Czapek-dox's agar develop restrictedly, attaining a diameter of 20–21 mm in 10 days at 25°C. They are flat, velvety, radial furrow, sometimes slightly raised at center, soft and thin.

The color of the colonies is brownish white to white at first, becoming pale orange. Exudates are not produced. Agar is pale yellow orange. The reverse of the colonies is pale yellow orange.

2. Physiological properties

Optimal growth on glucose agar: pH 2–7, 25°–30°C

Range of growth on glucose agar: pH 2–7, 15°–37°C

The characteriatics of the strain were compared with the references of H. L. Barnett, "Illustrated Genera of Imperfect Fungi", Burgess Publishing Company, Minneapolis (1960) and of G. L. Barron, "The Genera of Hyphomycetes from Soil", The Williams and Wilkins Co., Baltimore (1968), and the new strain is considered to belong to genus Cladosporium. The strain does not belong to genus Hyalodendron, because conidiophores of the strain of genus Hyalodendron are straight and not fragile, but not fusiform.

When compared with known strains of Cladosporium, there is no species corresponding to the new strain. Accordingly, the new strain is considered a new species, Cladosporium sp.

When compared with *C. herbarum* and *C. cladosporioides*, top of blastospore of the new strain is loosely crowded, whereas the same of *C. herbarum* is variable and that of *C. cladosporioides* is densely crowded. Furthermore, as to color of blastospores, the new strain is hyaline, whereas both of the known strains are pale brown.

The culture media for producing the peptidase are conventional and contain an assimilable carbon source, an assimilable nitrogen source, inorganic salts and minor organic nutrients.

The assimilable carbon sources include saccharides, such as glucose, sucrose, dextrins, and starch, and organic acids, such as acetic acid and citric acid. The assimilable nitrogen sources include natural organic substances, such as milk casein, soybean protein, peptone, meat extract, amino acid mixture, and corn steep liquor, and ammonium salts, such as ammonium sulfate and ammonium succinate. The inorganic salts are phosphates, magnesium salts, calcium salts, and so on.

The cultvation is carried out for 15 to 72 hours under aerobic conditions, while the pH is kept at 2 to 7, preferably 4 to 7. The temperature is maintained at 15° to 40°C, preferably 25° to 34°C, and the aeration is carried out either by shaking or by aerating with stirring (1/20–1/1 v/v, 100–500 r.p.m.).

After the cultivation, most of the peptidase is accumulated intracellularly. The peptidase may be used in the intracellular form, such as the culture broth, wet cells and freeze-dried cells.

When the peptidase is to be extracted from the cells, the cells are recovered from the cultured broth by centrifuging or by filtering. The cells recovered are suspended in water in an amount of 2–15 g/dl by weight of dry cell material, and after the pH of the suspension is adjusted to 6–8, the suspension is kept at 10° to 40°C for 3 to 20 hours. Thereafter, the cells are removed by centrifuging or filtering, and a supernatant containing a large portion of the peptidase is obtained.

The peptidase is precipitated from the supernatant by adding inorganic salts such as ammonium sulfate, and/or water miscible organic solvents such as isopropanol. The precipitate is recovered by filtering or centrifuging, followed by freeze-drying or vacuum drying. The leucineaminopeptidase activity of the dried powder is 200–800 units per gram.

The total peptidase activity was determined in the following manner. A 10% solution of milk casein was mixed with 150 units/ml of alkaline protease produced by Bacillus subtilis and digested for 24 hours at pH 8–10 at 50°C. The digestion product (T—N*¹ 1.40 g/dl, F—N*²/E—N*³ = 22%, the mean peptide bond length 4.2, the content of amino acids less than 5%) and the peptidase were placed in 0.1M phosphate buffer solution of pH 7, kept at 37°C, and the increase in amino groups was determined by the trinitrophenylation method (Satake et al., J. Biochem. (Japan), 47, 654 (1960)). One unit of peptidase activity was defined as producing 1 micro mole of amino group per minute.

*1 Total nitrogen content determined by Kjeldahl's method
*2 Nitrogen content determined by formol titration or trinitrophenylation
*3 (Total nitrogen content)-(nitrogen content of ammonium)

The leucineaminopeptidase activity was determined as follows: L-leucineparanitroanilide was employed as the substrate, and was hydrolyzed at pH 7 at 37°C. One unit of leucineaminopeptidase hydrolyzes 1 micro mole of the substrate per minute.

The peptidase produced in Example 1 hereinbelow has the following properties:

1. Substrate specifity

The peptidase produced by method of the invention is a leucineaminopeptidase and easily hydrolyzes substrates which are hydrolyzed by known leucineaminopeptidase, such as L-leucylglycylglycine. When a peptide mixture produced by hydrolysis of protein was hydrolyzed by the peptidase, there was no amino acid which was not readily released.

Since the peptidase cannot hydrolyze carbobenzoxy-L-glutamyl-Ltyrosine at pH 7, the peptidase has no carboxypeptidase activity.

2. Optimum pH

When 1mM L-leucineparanitroanilide in a Britton-Robinson buffer solution was hydrolyzed at 37°C for 10 minutes, the optimum activity of the peptidase was at pH 7 to 8. The optimum pH curve is shown in FIG. 1.

On the other hand, when a peptide mixture prepared by hydrolysis of milk casein as described above was hydrolyzed, the optimum activity was at pH 6.5 to 7.5.

3. pH Stability

When the peptidase was kept in a Britton-Robinson buffer solution at 50°C for 30 minutes, the residual activity of leucineaminopeptidase was as shown in FIG. 2, the peptidase being stable at pH 6 to 7.5.

4. Thermal stability

When the peptidase was kept in Brittton-Robinson buffer solution of pH 7 at 45°C for 60 minutes, the residual leucineaminopeptidase activity was 80%. After heating at 50°C for 30 minutes, the residual leucineaminopeptidase activity was 50%.

5. Inhibition

When 1mM cobalt ion was added to a Britton-Robinson buffer solution (pH 7) of the peptidase, the leucineaminopeptidase activity was increased to twice the initial activity. On the other hand, when 1mM EDTA was added, the activity was reduced to 50% of the initial activity.

The peptidase of the invention is highly active, and as shown in Table 1, glutamic acid, aspartic acid, proline, glycine and lysine are produced in high yields, while they are released in unsatisfactory yields by known peptidases.

Table 1

| Amino Acid | g/E-N | Amino Acid | g/E-N | Amino Acid | g/E-N |
|---|---|---|---|---|---|
| Trp | Tr | Ser | 0.42 | Met | 0.20 |
| Lys | 0.72 | Glu | 1.30 | Ile | 0.40 |
| His | 0.19 | Pro | 0.91 | Leu | 0.59 |
| Arg | 0.10 | Gly | 0.19 | Tyr | 0.06 |
| Asp | 0.29 | Ala | 0.29 | Phe | 0.32 |
| Thr | 0.34 | Val | 0.49 | Total | 6.81 |

The data of Table 1 were obtained from the protease digestion product of milk casein described above. 20 U/ml of the peptidase powder prepared in Example 1 were added to the digestion product, and the reaction was carried out at pH 7 at 37°C for 24 hours.

The reaction mixture: T—N 2.03g/dl, NH₃—N 0.55g/dl, E—N 1.48g/dl, F—N 1.46g/dl (by formol titration), F—N 1.32g/dl (by trinitrophenylation)

Table 2 shows a comparison of the activity of the peptidase prepared in Example 1 with that of a commercial peptidase "Protease Amano A" (Amano Seiyaku Co.) produced by *Aspergillu s oryzae*, which is considered the strongest known peptidase.

Table 2

| | The peptidase of the invention | "Protease Amano A" |
|---|---|---|
| Total Peptidase ACtivity towards Peptide Mixture | 380 | 110 |
| Leucineaminopeptidase Activity | 360 | 350 |

Table 3 indicates the yields of various amino acids when an alkaline protease digestion product of soy bean protein was hydrolyzed with the new peptidase and when hydrolyzed with Protease Amano A.

Table 3

| Amino Acid | The peptidase of the invention Yield (mg/dl) | | | "Protease Amano A" Yield (mg/dl) | | |
|---|---|---|---|---|---|---|
| | (A) Hydrolysis with enzyme | (B) Hydrolysis with HCl | (A)/(B) % | (A) Hydrolysis with enzyme | (B) Hydrolysis with HCl | (A)/(B) % |
| Trp | Tr | Tr | — | — | — | — |
| Lys | 506 | 594 | 85 | 600 | 726 | 83 |
| His | 130 | 155 | 83 | 107 | 151 | 71 |
| Arg | — | 18 | — | — | 22 | — |
| Asp | 552 | 704 | 63 | 205 | 688 | 30 |
| Thr | 215 | 247 | 86 | 160 | 237 | 68 |
| Ser | 417 | 295 | ND*1) | 313 | 282 | ND*1) |
| Glu | 915 | 1,053 | 87 | 523 | 1,021 | 51 |
| Pro | 405 | 422 | 96 | 134 | 360 | 37 |
| Gly | 201 | 252 | 80 | 88 | 260 | 34 |
| Ala | 211 | 238 | 89 | 159 | 226 | 70 |
| Val | 272 | 292 | 94 | 236 | 284 | 83 |
| Met | 86 | 60 | ND*1) | 94 | 56 | ND*1) |
| Ileu | 244 | 265 | 92 | 179 | 260 | 69 |
| Leu | 410 | 422 | 97 | 372 | 432 | 86 |
| Tyr | 8 | 21 | 39 | 28 | 53 | 53 |
| Phe | 229 | 237 | 97 | 210 | 238 | 88 |
| Total | 4,801 | 5,276 | 91 | 3,408 | 5,296 | 64 |
| The reaction mixture (g/dl) | T - N (g/dl) | | 0.93 | | | 0.95 |
| | $NH_3$ - N (g/dl) | | 0.15 | | | 0.18 |
| | E - N (g/dl) | | 0.78 | | | 0.77 |
| | F - N by Formol Titration (g/dl) | | 0.67 | | | 0.56 |
| | F – N by Trinitro phenylation (g/dl) | | 0.65 | | | 0.53 |

*1)Not determined because, the amino acid is further decomposed by HCl.

The reaction conditions: 100Ml of alkaline protease digestion product of soy bean protein (T—N 0.94g/dl, F—N/E—N = 25%, the mean peptide bond length 4.0, the content of amino acids less than 5%) were prepared, and mixed with 0.55g of the peptidase powder prepared in Example 1 or 0.6g of Protease Amano A. Ten grams of NaCl were added to the solution, the reaction was carried out at pH 7 at 37°C for 7 days, and the reaction mixture was filtered.

For acid hydrolysis, soy bean protein was hydrolyzed in 6NHCl at 110°C for 24 hours.

The invention is further illustrated by the following Examples. The peptidase activity reported in the Examples is leucineaminopeptidase activity.

EXAMPLE 1

Thirty liters of culture medium containing:

| | | |
|---|---|---|
| Glucose | 7 | g/dl |
| Milk casein | 1.5 | g/dl |
| Soy bean protein | 1.5 | g/dl |
| Corn steep liquor | 1 | ml/dl |
| $KH_2PO_4$ | 0.25 | g/dl |
| $MgSO_4.7H_2O$ | 0.02 | g/dl |
| pH 6.0 | | | were prepared, placed in a 70 liter jar fermenter, and sterilized at 120°C for 30 minutes.

The medium was inoculated with Cladosporium sp. FERM P-801 which had previously been cultured in a liquid culture medium (glucose 5g/dl, peptone 1.5g/dl, yeast extract 0.5g/dl, $KH_2PO_4$ 0.25g/dl, $MgSO_4.7H_2O$ 0.02g/dl, pH 6.5), and cultured at 31°C for 48 hours with stirring (350 r.p.m.) and aerating (1/4 v/v). Peptidase activity of the culture broth was found to be 2.2 units/ml.

The microbial cells in the broth were collected by centrifuging, and 6.3kg of wet cells (moisture content 80%) containing 10 units/g of peptidase activity were obtained. The yield was 95%. Peptidase activity of the supernatant was 0.1 unit/ml.

The wet cells were suspended in 4l of 0.1M phosphate buffer solution of pH 6.5, and stirred at 37°C for 5 hours. The cell residue was removed by centrifuging, and 7.2l of the supernatant containing 6.6 units peptidase activity per milliliter were obtained (yield; 72%).

4.8Kg of ammonium sulfate (0.9 saturation) were added to the supernatant, the mixture was allowed to stand overnight at 4°C, and the precipitate formed was collected. The precipitate was dissolved in 600ml of 0.05M phosphate buffer solution (pH 7.0), dialyzed overnight at 4°C against the same buffer solution, and lyophilized to yield 125g peptidase powder containing 360 units peptidase activity per gram (yield; 68.5%).

EXAMPLE 2

Cladosporium sp. FERM P-2447 was cultured in the same way as in Example 1, and a culture broth containing 2.1 units/ml of peptidase activity was obtained. Peptidase activity of the culture filtrate was 0.15 units/ml.

Thirty liters of the culture broth were worked up as in Example 1, and 135g of peptidase powder containing 290 units/g of peptidase activity was recovered (yield; 62%).

What is claimed is:

1. A method of preparing peptidase capable of hydrolyzing a peptide into the constituent amino acids, which comprises culturing a peptidase producing strain of Cladosporium in an aqueous culture medium containing assimilable sources of carbon and nitrogen, inorganic salts, and minor organic nutrients until said peptidase accumulates in the culture, and recovering said accumulated peptidase.

2. A method as set forth in claim 1, wherein said strain is Cladosporium sp. FERM P-801 or Cladosporium sp. FERM P-2447.

3. A method as set forth in claim 2, wherein said recovering comprises:
   a. separating the cells from the culture broth;
   b. suspending the separated cells in water in an amount of 2–15 g/dl by weight of dry cell material at pH 6–8;
   c. keeping the resulting suspension at 10°–40°C for 3–20 hours;
   d. removing the residual cell material from the suspension; and
   e. recovering the peptidase from the cell-free liquid.

4. A method as set forth in claim 1, wherein said strain is Cladosporium sp. EFRM P-801.

5. A method as set forth in claim 1, wherein said peptidase is recovered from the cells of said strain.

* * * * *